United States Patent [19]

Caillouette

[11] Patent Number: 5,554,160
[45] Date of Patent: Sep. 10, 1996

[54] UTERUS MANEUVERING METHOD

[76] Inventor: James C. Caillouette, 685 Oak Knoll Circle, Pasadena, Calif. 91106

[21] Appl. No.: 447,347

[22] Filed: May 23, 1995

[51] Int. Cl.[6] .................................................. A61B 17/42
[52] U.S. Cl. ........................................... 606/119; 606/193
[58] Field of Search ............................... 606/119, 1, 193

[56] References Cited

U.S. PATENT DOCUMENTS

| | | |
|---|---|---|
| 3,861,380 | 1/1975 | Chassagne et al. . |
| 4,000,743 | 1/1977 | Weaver . |
| 4,085,756 | 4/1978 | Weaver . |
| 4,430,076 | 2/1984 | Harris . |
| 4,703,241 | 10/1987 | Suzuki ............................ 318/599 |
| 4,775,362 | 10/1988 | Kronner . |
| 4,883,057 | 11/1989 | Broderick . |
| 4,929,949 | 5/1990 | Yamamoto et al. .............. 341/176 |
| 5,150,027 | 9/1992 | Suzuki ............................ 318/581 |
| 5,190,538 | 3/1993 | Hussein et al. . |
| 5,209,754 | 5/1993 | Ahluwalia . |
| 5,237,985 | 8/1993 | Hodgson et al. . |
| 5,382,252 | 1/1995 | Failla et al. . |
| 5,395,391 | 3/1995 | Essig et al. . |
| 5,409,496 | 4/1995 | Rowden et al. . |

*Primary Examiner*—Robert A. Hafer
*Assistant Examiner*—Benjamin Koo
*Attorney, Agent, or Firm*—William W. Haefliger

[57] ABSTRACT

A uterus maneuvering method involving the use of a lengthwise elongated boom, and a strut carried at one end of the boom to be pivoted relative to the boom, the strut and boom adapted to be inserted via the vaginal canal to locate the strut to project in the uterine cavity; actuator structure associated with the boom and strut, manipulable for effecting controlled pivoting of the strut; and control structure manipulable for controlling the actuator structure, and including a servo system having an extra-corporeal manual control structure, for coupling between the manual control structure and actuator structure, the coupling including electrical signal transmission structure.

25 Claims, 2 Drawing Sheets

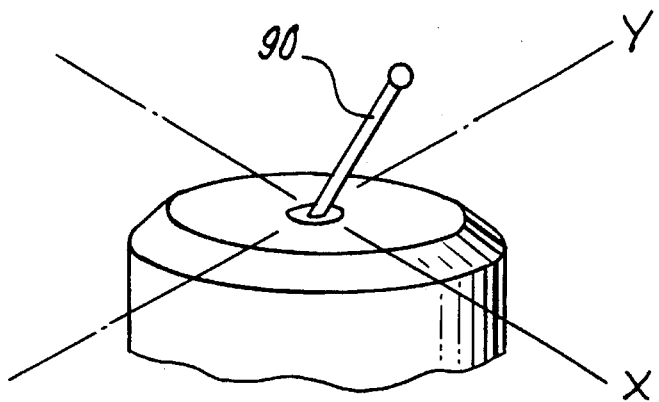
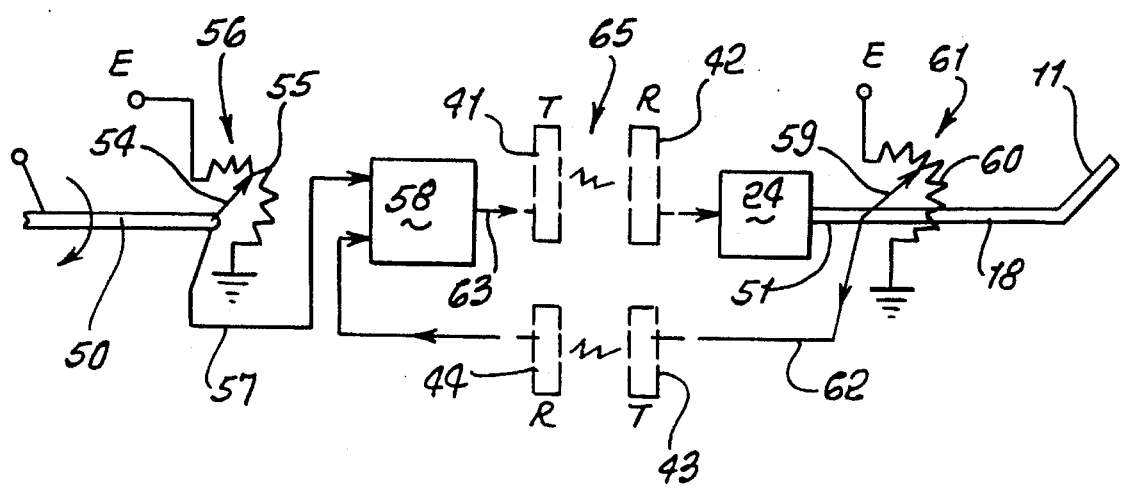

UTERUS MANEUVERING METHOD

BACKGROUND OF THE INVENTION

This invention relates generally to uterus maneuvering apparatus and method, and more particularly, to automatically controllable apparatus responsive to remote control means to manipulate or maneuver a uterus, and method for effecting such remote control. Associated means to inject fluid into the uterus and oviducts, is or may be provided.

Manipulation or maneuvering of the uterus is desired, as during laparoscopic examination. In the past, mechanical devices were used for this purpose, and employed handles and triggers that were manually operated immediately outside the patient's body, the actual manipulation tip having been inserted via the vagina and cervix. This required an assistant or nurse to manually manipulate the instrument, while receiving oral instructions from the surgeon in operating position over the patient's abdomen.

There is need for improved apparatus and method of use thereof, whereby the surgeon can himself directly manipulate the instrument, to maneuver the uterus, while he stands in operating position, and while he can observe the uterus position, as via an observation screen. There is also need for associated apparatus to inject fluid (for treatment, examination or identification) into the uterus and oviducts.

SUMMARY OF THE INVENTION

It is a major object of the invention to provide improved uterine maneuvering apparatus and method meeting the above need. Basically, the apparatus of the invention comprises, in combination:

a) a lengthwise elongated boom, and a strut carried at one end of the boom to be pivoted relative to the boom, the strut and boom adapted to be inserted via the vaginal canal to locate the strut to project in the uterine cavity, b) actuator means associated with the boom and strut for effecting controlled pivoting of the strut, and c) control means for controlling the actuator means, and including a servo system having an extra-corporeal manual control means, for coupling between the manual control means and actuator means, the coupling including electrical signal transmission means.

Accordingly, the surgeon may himself operate the control means, as for example via a joystick, to maneuver the uterus.

It is another object of the invention to provide such coupling between the manual control means and the actuator means, as for example in the form of a radio signal transmission link, or electrical wiring.

A further object includes the provision of support structure for the boom to orient the boom in selected position with the strut inserted into the uterus for pivoting therein; such support structure may typically carry the boom for pivoting about an axis extending lengthwise at the boom.

Yet another object includes the provision of the actuator means to include:

i) a first electrically responsive actuator to affect pivoting of the strut about a first axis, and ii) a second electrically responsive actuator to effect pivoting of the strut about a second axis.

Further objects include the provision of first manual control movable to effect servo-controlled operation of the first actuator; and second manual control means to effect servo-controlled operation of the second actuator. Such controls may take the form of at least one joystick which the surgeon can operate at a location outside the patient's body, and remotely from the boom and strut instrumentation. In addition, auxiliary means may be employed, including an inflatable balloon carried by the strut to be remotely controllably inflated; and a fluid injection duct may extend along the boom, for remotely controllable injection into the uterus or oviducts, of fluid, as referred to above.

These and other objects and advantages of the invention, as well as the details of an illustrative embodiment, will be more fully understood from the following specification and drawings, in which:

DRAWING DESCRIPTION

FIG. 2 is a representation of a single joystick rotatable about two axes; and

FIG. 3 is a simplified schematic drawing of a servo system.

DETAILED DESCRIPTION

Figure 1:
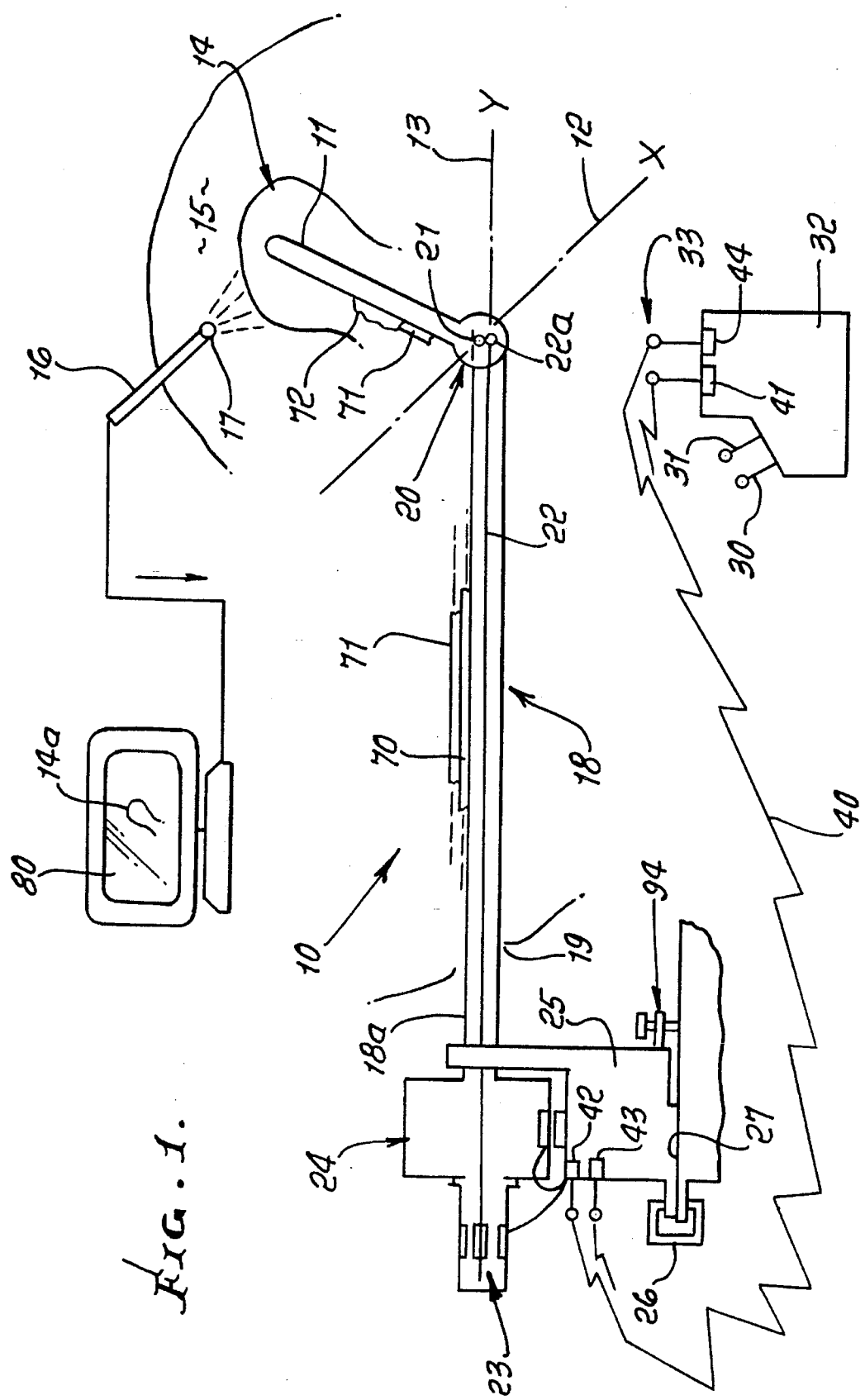
FIG. 1 is a schematic representation of a system in which the invention is embodied.

In FIG. 1, the instrument 10 includes a tip in the form of a strut 11 movable about two axes 12 and 13 (X and Y axes) for maneuvering the uterus 14 into which it has been inserted. The patient's abdominal cavity is seen at 15, and a laparoscope 16 projects into that cavity. A light source 17, on or associated with the laparoscope, illuminates the pelvic organs. The surgeon or physician normally stands adjacent the patient to look downwardly toward 16 and 17; and he is, therefore, at a distance, or remote from, the end 18a of the longitudinally elongated, narrow housing or boom 18 of the uterine manipulator projecting into and from the vaginal entrance 19.

Boom 18 supports strut 11, for rotation about axes 12 and 13; and merely as illustrative, a rotor 20 is pinned at 21 to the end of the boom to pivot about X axis 12, and one end of the strut 11 is connected to the rotor to rotate therewith. An elongated actuator member 22 is connected with the rotor at 22a, in offset relation to 21, i.e., to "crank" the rotor 20 about axis 12, as member 22 is moved longitudinally endwise. FIG. 1 shows member 22 as a link extending protectively within boom 68. A linear actuator 23 is connected to member 22, at the end of the instrument outside the patient's body. Actuator 23 is in turn carried by the rotary actuator 24 supported for rotation by a base 25. The latter is adjustably fixed in position by a clamp 26 or other means holding base 25 to a table 27. Other devices to support actuator 24 for rotation about axis 13 may be employed.

Actuator 24 is connected to the boom 18 to support it for rotation about axis 13, as actuator 24 controllably rotates, clockwise or counterclockwise, about Y axis 13.

FIG. 1 shows two joysticks 30 and 31 supported on a carrier 32, as at the location of the physician. The two joysticks are pivotally supported, as at 30a and 31a, and are pivotable to control the strut rotation about X axis 12, (i.e., up and down) and boom rotation about Y axis 13.

A servo system is provided, as indicated at 33, for coupling between the manual control means (i.e., joysticks 30 and 31, for example) and the actuator means (i.e., 23 and 24, for example). The coupling includes electrical signal transmission means, indicated at 40, in the form of a radio signal transmission link.

Radio transmitter 41, at the manual control location, and receiver 42, at the location of the actuators, transmits position control signals or data for reception at the actuators, to position the latter. AM or FM may be used, such transmission and reception circuitry being known. A feedback signal transmitter 43 at the location of the actuators transmits feedback signals for reception by a receiver 44 at the location of the control joysticks.

FIG. 3 shows one basic form of an analog servo system, with a joystick-controlled input shaft 50, and an output-controlled shaft 51 (rotary or linear actuator), which corresponds to the output member of the actuator 23 or 24. A wiper 54 on the shaft 50 variably engages a resistance 55 of a potentiometer 56, to derive a position control signal on lead 57 fed to comparator 58. Similarly, a wiper 59 on the actuator output shaft 51 is moved by the latter to variably engage a resistance 60 of a potentiometer 61, to derive a shaft position-determined feedback signal on the feedback loop 62, and also fed to the comparator 58. The differencing output of the latter is transmitted at 63 to the actuator 24 to drive it forward or backward until the controlled position of shaft 51 (i.e., of boom 18) corresponds to the controlling position of the joystick. The radio communication link, including circuitry, is indicated at 65.

A similar servo is provided for the second joystick controlling the position of the actuator 23 that angularly positions the strut 11 in the uterus. Suitable DC amplification may be provided in association with the actuators to drive step-motors, or pulse motors, associated with such actuators in response to control signal reception.

The radio link at 65 may be replaced by elongated, flexible wires that extend to the actuators 23 and 24, from the comparator; and in that event, a DC amplifier may be associated with the comparator. Analog or digital servo systems may be employed.

FIG. 1 also shows a duct 70 extending along the boom 18 for controllably conducting examination or treatment fluid to the uterus. For example, a colored fluid (such as methylene blue, in saline aqueous solution) can be injected for observation. Similarly, an inflation air duct 71 may extend along the boom 18 for controllably conducting such air or gas to a balloon 72 at the middle of the strut, to be inflated in the uterus, as may be desired, for example to hold the apparatus element 11 positioned in the uterine cavity.

A CRT screen is shown at 80 to display the output of the laparoscope 16, i.e., showing the position of the uterus; and the surgeon may merely operate the joysticks to maneuver the uterus to desired position, as displayed at 14a on the screen. Scope 16 typically includes fiber optical elements, connected to the CRT or its circuitry.

FIG. 2 shows a single joystick 90 replacing the dual joysticks 30 and 31, to simplify operation and control. Joystick 90 rotates about dual axes indicated at X and Y, to control the two actuators. In FIG. 1, an adjustable support may be provided for base 25 to adjust along three perpendicular axes, for patient comfort. See for example adjustable jackscrew 94, to tilt the base, as for example relative to the patient undergoing examination.

A usable servo positioning control system, with radio link, is sold by Futaba Corporation of America, 4 Studebaker, Irvine, Calif. Such control systems are used to radio control model airplanes.

I claim:

1. In a uterus maneuvering method, the steps that include:
   a) providing a lengthwise elongated boom, and a strut carried at one end of the boom to be pivoted relative to the boom, and inserting the strut and boom via the vaginal cavity to locate the strut to project in the uterine cavity,
   b) providing actuator means associated with the boom and strut for effecting controlled pivoting of the strut, and providing a linkage to extend within the boom and to operatively connect between the actuator means and said strut,
   c) providing control means for controlling said actuator means, and including a servo system having an extracorporeal manual control means, for coupling between said manual control means and actuator means,
   d) and operating said servo system to maneuver the uterus,
   e) providing support structure for said boom, and orienting the boom in selected position in the birth canal with said strut inserted into the uterus for pivoting therein,
   f) and wherein said support structure is provided to carry the boom for pivoting about an axis extending lengthwise at the boom.

2. The method of claim 1 wherein said coupling includes a radio signal transmission link, and including transmitting radio signals in response to operation of said servo system.

3. The method of claim 1 wherein said coupling includes electrical wiring, and including transmitting electrical signals via said wiring, in response to operation of said servo system.

4. The method of claim 1 wherein said support structure includes a support housing from which the boom extends, and a support stand for said housing, and including controllably anchoring said support stand to orient the boom in said selected position.

5. The method of claim 1 wherein said actuator means is provided to include:
   i) a first electrically responsive actuator to affect pivoting of the strut about a first axis, and
   ii) a second electrically responsive actuator to effect pivoting of the strut about a second axis.

6. The method of claim 5 including coupling the second actuator to the boom to rotate the boom and strut about said second axis.

7. The method of claim 5 wherein said manual control means is provided to include a first manual control movable to effect servo-controlled operation of the first actuator.

8. The method of claim 7 wherein said manual control means is provided to include a second manual control movable to effect servo-controlled operation of the second actuator.

9. The method of claim 8 wherein said first and second manual controls are provided to include at least one joystick.

10. The method of claim 1 including providing an inflatable balloon carried by said strut to be inflated within the uterus, during maneuvering of the uterus in accordance with movement of the strut.

11. The method of claim 8 including providing a pressurization duct extending along the boom and to said balloon.

12. The method of claim 1 including providing a fluid injection duct extending along the boom and to the strut for injecting fluid into the uterus.

13. In a body tissue maneuvering method, the steps that include:
   a) providing a lengthwise elongated boom, and a strut carried at one end of the boom to be pivoted relative to the boom, and inserting the strut and boom in a body canal to extend to said body tissue,
   b) providing actuator means associated with the boom and strut for effecting controlled pivoting of the strut, and providing a linkage to extend within the boom and to operatively connect between the actuator means and said strut, c) providing control means for controlling said actuator means, and including a servo system having an extra-corporeal manual control means, for coupling between said manual control means and actuator means, said coupling including electrical signal transmission means, d) operating said servo system to maneuver said tissue, (e) and wherein said support structure is provided to carry the boom for pivoting about an axis extending lengthwise at the boom.

14. The method of claim 13 wherein said coupling includes a radio signal transmission link, and including transmitting radio signals in response to operation of said servo system.

15. The method of claim 13 wherein said coupling includes electrical wiring, and including transmitting electrical signals via said wiring, in response to operation of said servo system.

16. The method of claim 13 including providing support structure for said boom, orienting the boom in selected position in the birth canal with said strut inserted into the canal for pivoting therein.

17. The method of claim 16 wherein said support structure includes a support housing from which the boom extends, and a support stand for said housing, and including controllably anchoring said support stand to orient the boom in said selected position.

18. The method of claim 13 wherein said actuator means is provided to include:

i) a first electrically responsive actuator to affect pivoting of the strut about a first axis, and ii) a second electrically responsive actuator to effect pivoting of the strut about a second axis.

19. The method of claim 18 including coupling the second actuator to the boom to rotate the boom and strut about said second axis.

20. The method of claim 18 wherein said manual control means is provided to include a first manual control movable to effect servo-controlled operation of the first actuator.

21. The method of claim 20 wherein said manual control means is provided to include a second manual control movable to effect servo-controlled operation of the second actuator.

22. The method of claim 21 wherein said first and second manual controls are provided to include at least one joystick.

23. The method of claim 13 including providing an inflatable balloon carried by said strut to be inflated within the canal, for maneuvering body tissue in accordance with movement of the strut.

24. The method of claim 23 including providing a pressurization duct extending along the boom and to said balloon.

25. The method of claim 13 including providing a fluid injection duct extending along the boom and to the strut for injecting treatment fluid into the uterus.

* * * * *